(12) United States Patent
Mallin et al.

(10) Patent No.: US 9,345,540 B2
(45) Date of Patent: May 24, 2016

(54) CONTACT SPECIFIC RF THERAPY BALLOON

(71) Applicant: MEDTRONIC ABLATION FRONTIERS LLC, Minneapolis, MN (US)

(72) Inventors: George D. Mallin, Beaconsfield (CA); Timothy G. Laske, Shoreview, MN (US); Joseph Allen Knight, Kokomo, IN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 417 days.

(21) Appl. No.: 13/832,609

(22) Filed: Mar. 15, 2013

(65) Prior Publication Data

US 2014/0276712 A1 Sep. 18, 2014

(51) Int. Cl.
*A61B 18/18* (2006.01)
*A61B 18/14* (2006.01)
*A61B 18/02* (2006.01)
*A61B 18/00* (2006.01)
(Continued)

(52) U.S. Cl.
CPC .............. *A61B 18/1492* (2013.01); *A61B 18/02* (2013.01); *A61B 18/18* (2013.01); *A61B 2018/0022* (2013.01); *A61B 2018/00875* (2013.01); *A61B 2018/0212* (2013.01); *A61B 2018/126* (2013.01); *A61B 2018/1253* (2013.01); *A61B 2019/465* (2013.01)

(58) Field of Classification Search
CPC ........... A61B 18/18; A61B 2018/0022; A61B 2018/00875; A61B 2018/1253; A61B 2018/126; A61B 2019/465

USPC ....................................................... 606/25, 33
See application file for complete search history.

(56) References Cited

U.S. PATENT DOCUMENTS

| 5,398,683 A | 3/1995 | Edwards et al. |
| 5,617,854 A | 4/1997 | Munsif |
| 6,088,614 A | 7/2000 | Swanson |

(Continued)

FOREIGN PATENT DOCUMENTS

| EP | 1322377 B1 | 4/2005 |
| EP | 1383426 B1 | 12/2008 |

(Continued)

OTHER PUBLICATIONS

International Search Report and Written Opinion dated Jun. 17, 2014 for International Application Serial No. PCT/US2014/021552, International Filing Date: Mar. 7, 2014 consisting of 9 pages.

*Primary Examiner* — Niketa Patel
*Assistant Examiner* — Lindsey G Hankins
(74) *Attorney, Agent, or Firm* — Christopher & Weisberg, P.A.

(57) ABSTRACT

A catheter including a proximal end and a distal end. An expandable element coupled to the distal end is included, the expandable element including a proximal portion and a distal portion, the expandable element defining an exterior surface. A first plurality of electrodes coupled to the exterior surface of the distal portion of the expandable element are included, each of the first plurality of electrodes being selectively operable to transmit unipolar radiofrequency energy. A second plurality of electrodes coupled to the exterior surface of the proximal portion of the expandable element are included, each of the second plurality of electrodes being selectively operable to transmit bipolar radiofrequency energy.

10 Claims, 5 Drawing Sheets

(51) Int. Cl.
 *A61B 18/12* (2006.01)
 *A61B 19/00* (2006.01)

(56) References Cited

U.S. PATENT DOCUMENTS

| | | | |
|---|---|---|---|
| 6,091,993 | A | 7/2000 | Bouchier et al. |
| 6,738,673 | B2 | 5/2004 | Desai |
| 7,519,410 | B2 | 4/2009 | Taimisto et al. |
| 7,540,853 | B2 | 6/2009 | Hayzelden |
| 7,655,005 | B2 | 2/2010 | Bhola |
| 2002/0035361 | A1 | 3/2002 | Houser et al. |
| 2002/0188325 | A1 | 12/2002 | Hill et al. |
| 2005/0256521 | A1 | 11/2005 | Kozel |
| 2006/0235286 | A1* | 10/2006 | Stone et al. .......... 600/381 |
| 2007/0129720 | A1* | 6/2007 | Demarais et al. .......... 606/41 |
| 2008/0281391 | A1 | 11/2008 | MacAdam et al. |
| 2009/0012513 | A1 | 1/2009 | Utley et al. |
| 2009/0228003 | A1 | 9/2009 | Sinelnikov |
| 2009/0248014 | A1 | 10/2009 | Shachar et al. |
| 2009/0299355 | A1 | 12/2009 | Bencini et al. |
| 2011/0184400 | A1 | 7/2011 | Pageard |
| 2011/0270237 | A1* | 11/2011 | Werneth et al. .......... 606/20 |
| 2012/0035601 | A1 | 2/2012 | Wittenberger |
| 2012/0197243 | A1 | 8/2012 | Sherman et al. |
| 2013/0165923 | A1* | 6/2013 | Mathur .......... A61B 18/18 606/41 |

FOREIGN PATENT DOCUMENTS

| | | |
|---|---|---|
| WO | 9406349 A1 | 3/1994 |
| WO | 9634571 A1 | 11/1996 |
| WO | 9902096 A1 | 1/1999 |
| WO | 0122897 A1 | 4/2001 |
| WO | 02083196 A2 | 10/2002 |
| WO | 2005067668 A2 | 7/2005 |
| WO | 2006118725 A1 | 11/2006 |
| WO | 2009065042 A2 | 5/2009 |
| WO | 2009140067 A1 | 11/2009 |
| WO | 2010067360 A2 | 6/2010 |

\* cited by examiner

CONTACT SPECIFIC RF THERAPY BALLOON

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for tissue contact specific ablation therapy, and in particular, radiofrequency ablation.

BACKGROUND OF THE INVENTION

Minimally invasive devices, such as catheters, are often employed for medical procedures, including those involving ablation, dilation, and the like. In a particular situation, an ablation procedure may involve creating a series of lesions in order to electrically isolate tissue believed to be the source of an arrhythmia. Such lesions may be created using a variety of different energy transmission modalities, such as cryogenic freezing or heating with radiofrequency ("RF") energy.

Electrically driven RF ablation catheters typically include an arrangement of electrodes configured to contact tissue and apply RF energy thereto so that the tissue heats up due to resistive heating, creating an ablation lesion. Catheters or devices using cryogenic cooling may be used to lower the temperature of tissue, such as cardiac wall tissue, to an extent such that signal generation or conduction temporarily ceases and allows one to map or confirm that the catheter is positioned at a particular lesion or arrhythmia conduction site. Cryogenic catheters may also operate at lower temperatures for ablation treatment, e.g., to cool the tissue to a level at which freezing destroys the viability of the tissue, and, in the case of cardiac tissue, permanently removes it as a signal generating or signal conducting locus. Irrespective of the particular ablation modality employed, the treatment goal common to virtually all cardiac or other ablation treatments is to create an effective lesion and/or provide for the desired, controlled destruction of selected tissues.

However, typical RF ablation devices either include a basket or constellation type electrode array or a linear array in which all the electrodes operate to deliver RF ablation energy regardless of the position of a particular electrode on the array or basket. Thus, healthy tissue is sometimes ablated, electrodes that are not in contact with the target tissue are activated, and the efficiency of a particular ablation procedure is reduced. Such limited range of operation may necessitate lengthy treatment procedures involving many iterations of ablative lesion forming, and re-mapping or checking the quality of lesion or symptomatic presence prior to completing a treatment procedure. Such steps may require a lengthy amount of time to perform, thus exposing the patient to undesired risk.

Accordingly, there remains a need for medical devices and methods that achieve an extended range of thermal transfer while ablating tissue more effectively and to a greater depth.

SUMMARY OF THE INVENTION

The present invention advantageously provides a device, method, and system for identifying tissue contact points and ablating tissue in contact with electrodes at the tissue contact points. The medical device includes a catheter including a proximal end and a distal end. An expandable element coupled to the distal end is included, the expandable element including a proximal portion and a distal portion, the expandable element defining an exterior surface. A first plurality of electrodes coupled to the exterior surface of the distal portion of the expandable element are included, each of the first plurality of electrodes being selectively operable to transmit unipolar radiofrequency energy. A second plurality of electrodes coupled to the exterior surface of the proximal portion of the expandable element are included, each of the second plurality of electrodes being selectively operable to transmit bipolar radiofrequency energy.

In another embodiment, the method includes positioning a medical device having an expandable element proximate the target tissue region, the expandable element including a first plurality of electrodes coupled to a distal portion of the expandable element, and a second plurality of electrodes coupled to a proximal portion of the expandable element. Unipolar radiofrequency energy is transmitted from the first plurality of electrodes. An impedance from each electrode of the first plurality of electrodes is measured. Bipolar radiofrequency energy is transmitted from the second plurality of electrodes. An impedance from each electrode of the second plurality of electrodes is measured. The measured impedance from each electrode of the first plurality of electrodes and the second plurality of electrodes is compared. Tissue contact areas are identified based on the comparison. Tissue in contact with the expandable element is ablated based on the comparison.

In yet another embodiment, the system includes a medical device. The medical device includes: a catheter including a proximal end and a distal end; an expandable element coupled to the distal end, the expandable element including a proximal portion and a distal portion, the expandable element defining an exterior surface; a first plurality of electrodes coupled to the exterior surface of the distal portion of the expandable element, each of the first plurality of electrodes being selectively operable to transmit unipolar radiofrequency energy; a second plurality of electrodes coupled to the exterior surface of the proximal portion of the expandable element, each of the second plurality of electrodes being selectively operable to transmit bipolar radiofrequency energy. A control unit having a processor is included, the processor being operable to: transmit unipolar radiofrequency energy from the first plurality of electrodes; measure an impedance from each electrode of the first plurality of electrodes; transmit bipolar radiofrequency energy from the second plurality of electrodes; measure an impedance from each electrode of the second plurality of electrodes; compare the measured impedance from each electrode of the first plurality of electrodes and the second plurality of electrodes; identify tissue contact areas based on the comparison; and ablate tissue in contact with the expandable element based on the comparison.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
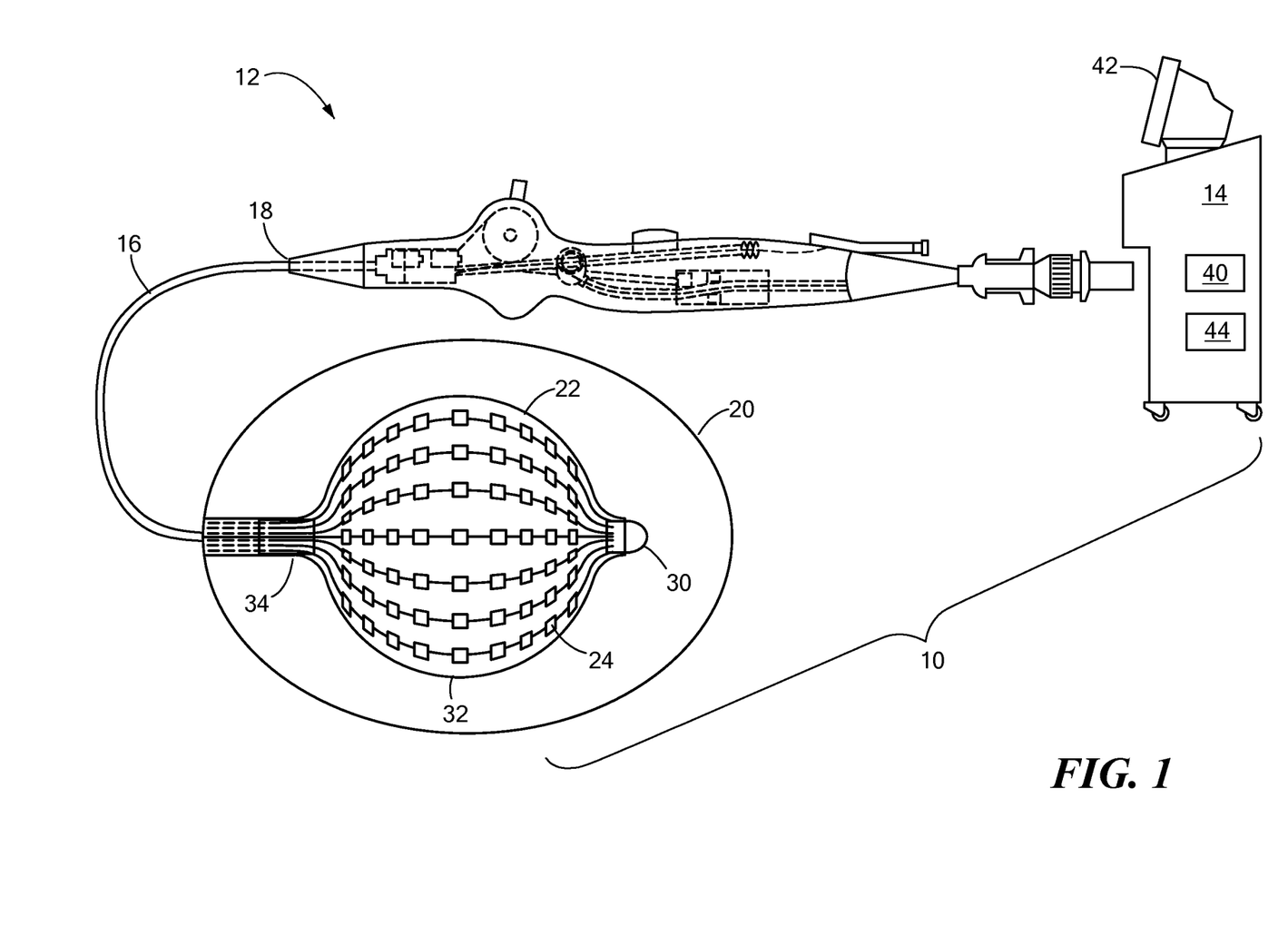
FIG. 1 is a side view of a medical system and device constructed in accordance with the principles of the present invention.

The present invention provides medical devices, systems and methods of use thereof to perform medical diagnoses and treatments including electrophysiological mapping, radiofrequency ablation, and cryogenic ablation. Referring now to the drawings in which like reference designators refer to like elements, there is shown in FIG. 1 an exemplary embodiment of a medical system for diagnosing and treating tissue, such as cardiac or other vascular tissue, designated generally as 10. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein may be included in a variety of different combinations or configurations without departing from the scope and spirit of the invention Referring now to FIG. 1, the system 10 generally includes a medical device 12 that may be coupled to a control unit or operating console 14. The medical device 12 may include an elongate body 16 passable through a patient's vasculature and/or proximate to a tissue region for diagnosis or treatment, such as a catheter, sheath, or intravascular introducer, or a combination thereof. The elongate body 16 may define a proximal portion 18 and a distal portion 20, and may further include one or more lumens disposed within the elongate body 16 thereby providing mechanical, electrical, and/or fluid communication between the proximal portion 18 of the elongate body 16 and the distal portion 20 of the elongate body 16, as discussed in more detail below.

The medical device 12 may further include a diagnostic or treatment assembly 22 on the distal portion 20 of the elongate body 16 for assessing or measuring a property or characteristic of a tissue site (e.g., cardiac signal mapping, tissue composition assessments, tissue contact assessment, or the like) and/or for delivering or otherwise transmitting a therapeutic or diagnostic signal or energy to a tissue site (e.g., electrical energy delivery, tissue ablation, cardiac pacing, or the like). The treatment assembly 22 may deliver, for example, radiofrequency energy, cryogenic therapy, or the like to a tissue area in proximity to the distal portion 20 of the medical device 12.

The treatment assembly 22 may include a cryogenic element, tip, or expandable element 24, which may include one or more balloons. A compliant balloon in an expanded configuration may have any suitable shape, such as for example a spherical shape or a shape with a distal portion 30, an intermediate portion 32, and a proximal portion 34. The terms "proximal" and "distal" are generally understood in the medical device industry. For example, a catheter handle may be at a proximal end, and various components for treating a patient may be at or near a distal end. In addition, the terms "proximal" and "distal" may refer to either absolute positions on the medical device, or may refer to relative positions along a longitudinal axis defined by the medical device, or along a geometric path of advancement, retraction or position.

If the expandable element 24 is a double balloon configuration, the inner balloon may be in fluid communication with an inflation lumen so that it inflates to an expanded shape, and the outer balloon follows that expanded shape. The outer balloon may be provided for additional safety or leak detection. Alternatively, different types of expandable members 24 may be provided, including for example an expandable armature or wireframe with a sheath or cover. The wall of the expandable element 24 may be very thin, or formed with one or more suitable materials to achieve high heat transfer rates. Examples of materials that may be used to construct such as an expandable element 24 of a treatment assembly 22 are polymers, plastics, or a mixture or layers thereof. An injection lumen and an exhaust lumen are in fluid communication with the interior of the expandable element 24 or balloon to define a fluid flow path there through, facilitating the delivery and/or circulation of a refrigerant or coolant such as a cryogenic fluid or an inflation fluid such as a gas or saline.

Figure 2:
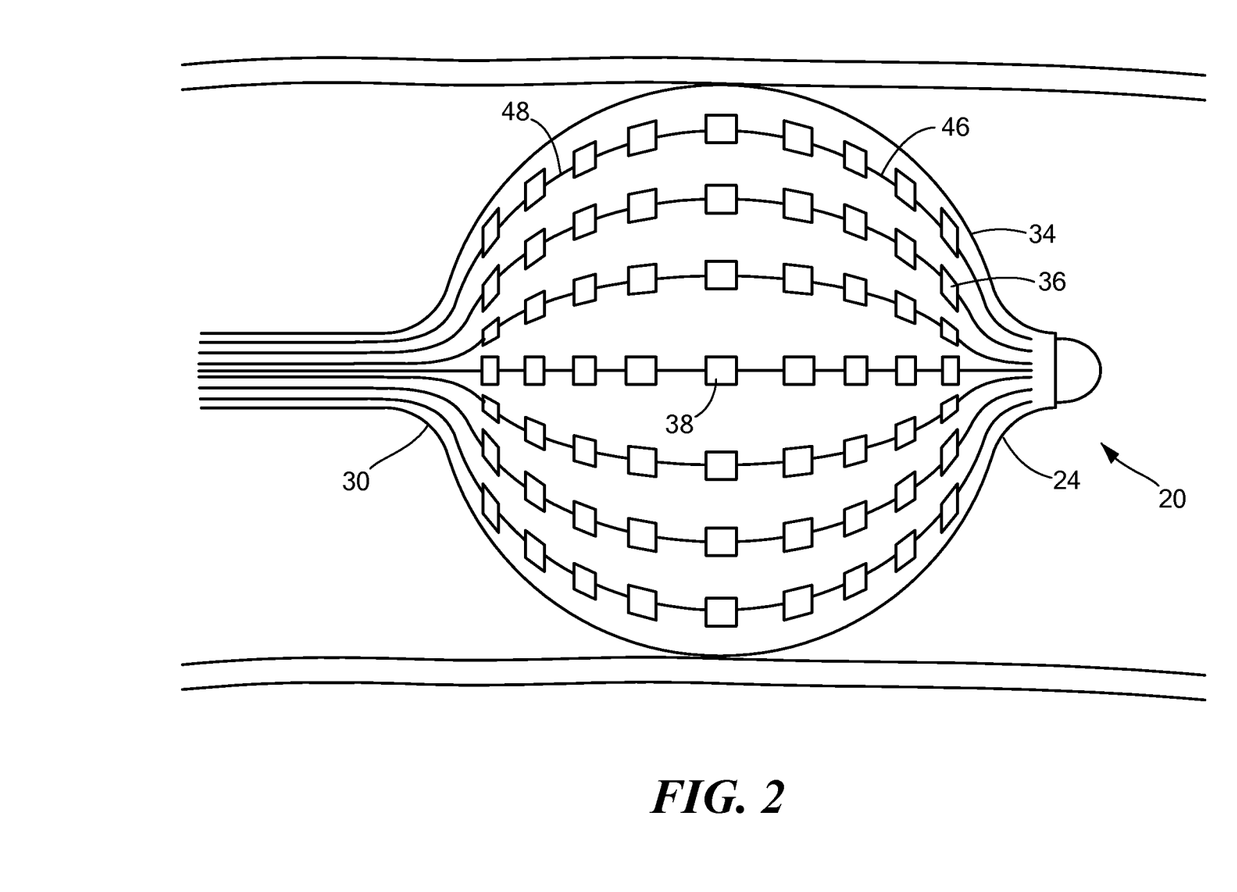
FIG. 2 is another side view of the medical device of FIG. 1 disposed within a vein.

Referring now to FIGS. 1 and 2, the treatment assembly 22 may include a first plurality of electrodes 36, or electrically conductive portions of electrodes, coupled or otherwise affixed to or proximate the distal portion 30 of the expandable element 24, and a second plurality of electrodes 38 electrodes coupled or otherwise affixed to or proximate the proximal portion 34 of the expandable element 24. If the expandable element 24 is a single balloon, the electrodes 36, 38 may be on an outer surface of the balloon. If the expandable element 24 is a double balloon treatment assembly, the electrodes 36, 38 may be on the outer balloon.

The electrodes 36, 38 may include variations in their number, arrangement, configuration, or shape and may be constructed from conductive materials such as silver, platinum or gold. The electrodes 36, 38 may be coupled to or otherwise be in electrical communication with a power delivery and/or measurement source 40, in the control unit 14 operable to deliver or measure a characteristic of a particular energy (such as unipolar and/or bipolar radiofrequency ablation signal, a cardiac pacing signal, impedance voltage, or other therapeutic or diagnostic signal, and/or properties thereof, for example) to the medical device 12 during a designated medical procedure. The control unit 14 may further include a display 42 operable to display the measured characteristics recorded from the treatment assembly 22 and a fluid inflation source 44, such a cryogenic fluid, saline, or gas source in fluid communication with the inflation and exhaust lumens and the expandable element 24.

Figure 3:
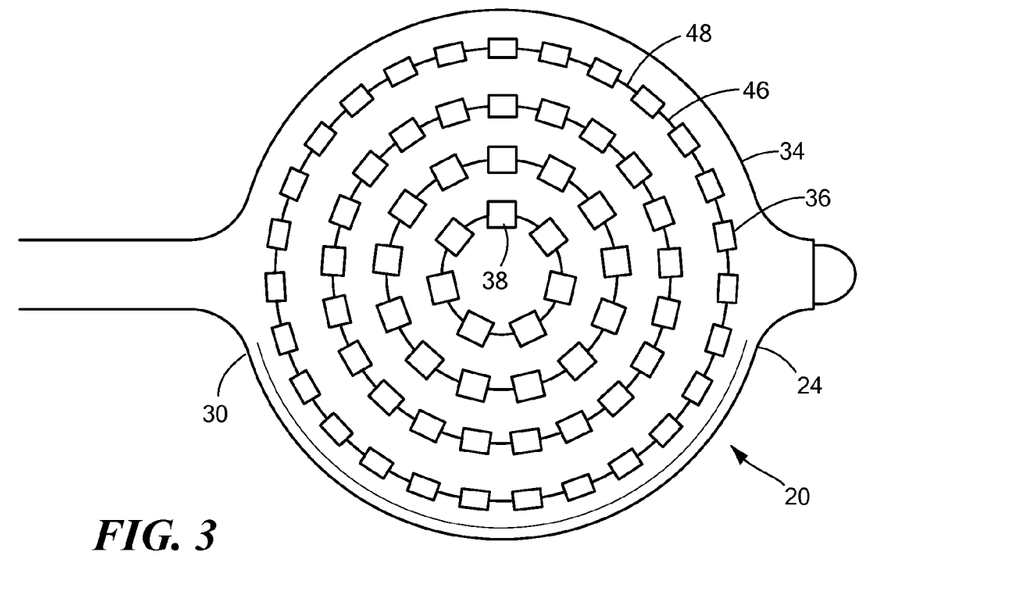
FIG. 3 is a side view of the medical device of FIG. 2 with a different arrangement of electrodes on the expandable element's surface.

Referring now to FIGS. 2 and 3, the grid-like arrangement of the electrodes 36, 38, and the energy modality delivered by the electrodes 36, 38 may vary depending on the particular procedure performed in order to determine tissue contact points. For example, in the configuration shown in FIG. 2, the first plurality of electrodes 36 are coupled to the distal portion 34 of the expandable element 24 and are operable to transmit unipolar RF energy from each electrode 36 in the first plurality of electrodes 36 to a reference electrode (not shown) to measure far-field impedances and, if desired, to ablate tissue in contact with the electrodes 36. The second plurality of electrodes 38 are coupled to the proximal portion 30 and/or the intermediate portion 32 of the expandable element 24 and are operable to transmit bipolar RF energy between two electrodes 38 to measure near-field impedances and, if desired, to ablate tissue in contact with the electrodes 38. Each electrode 36 or 38 or several of the electrodes 36 or 38, may be connected to one or more wires 46 or conductive strip, which is connected to the RF generator 40 such that a single electrode 36 or 38, or a plurality of the electrodes 36 or 38 may be activated by the control unit 14. In particular, a series of electrodes 36 and/or 38 may be arranged in an array of electrodes 48 such that a particular electrode array 48 may be selectively activated for a particular mapping or ablation procedure. Each electrode 36 or 38 in the array 48 may be selectively and individually activated depending on the position of the expandable element 24 with respect to the tissue to be treated, as discussed in more detail below.

Figure 5:
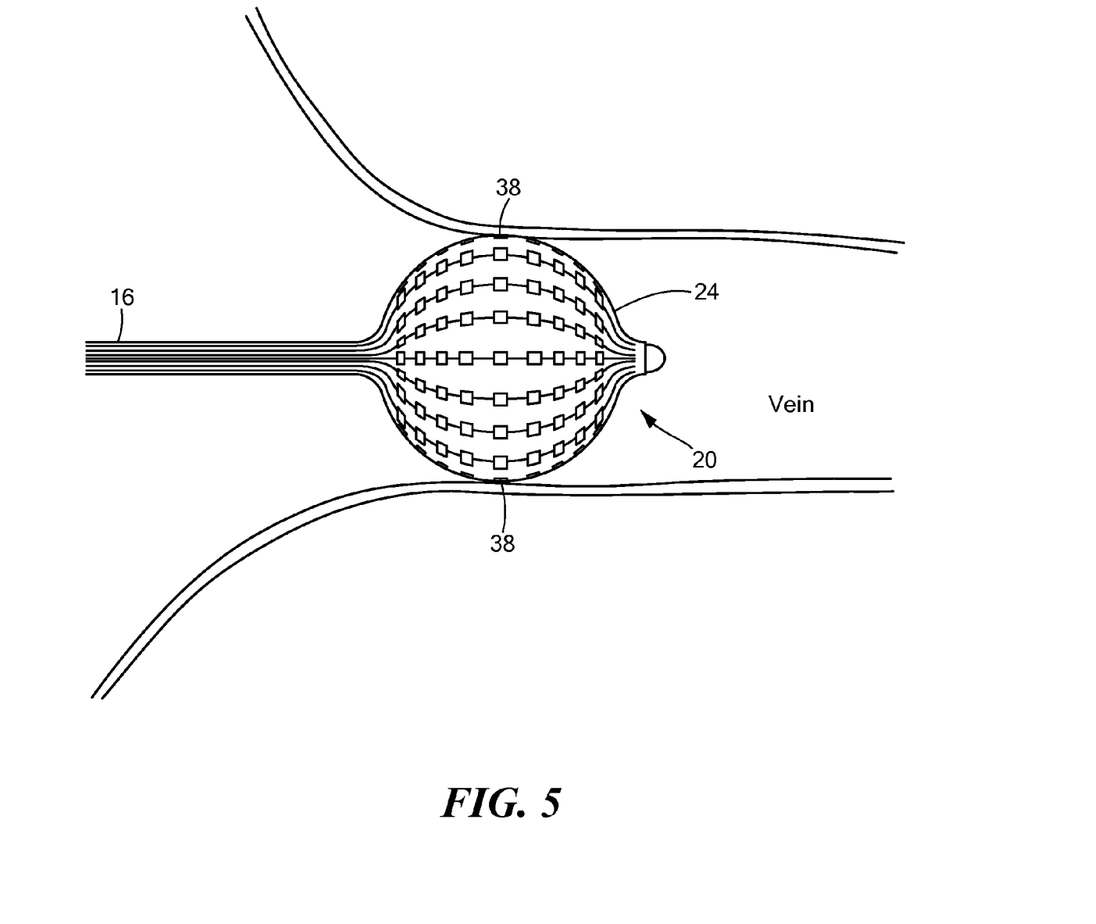
FIG. 5 is the medical device shown in FIG. 1 with arrays of electrodes.

The positioning and arrangement of the electrodes 36, 38 and electrode arrays 48 may vary depending on in what orifice of the body a tissue is to be examined and/or treated. For example, in the configuration shown in FIG. 5, the arrays 48 extend longitudinally from the proximal portion 30 to the distal portion 34, and in the configuration shown in FIG. 3 the arrays 48 extend radially out from the intermediate portion 32 of the expandable element 24. The spacing between each of the electrodes 36, 38 may be uniform or variable. For example, the spacing between the electrodes 36 may be smaller whereas the spacing between the electrodes 38 may be larger, or vice versa. In an exemplary configuration, the electrodes 36, 38 span substantially the entire surface of the expandable element 24. In other configurations, the electrodes 36, 38 are disposed at the distal portion 34 and proximal portion 30 with portions of the expandable element 24 having portions of its surface not including electrodes 36 or 38. The electrodes 36, 38 may further be identical in size and may further be operable to selectively transmit both bipolar and unipolar radiofrequency.

Figure 4:
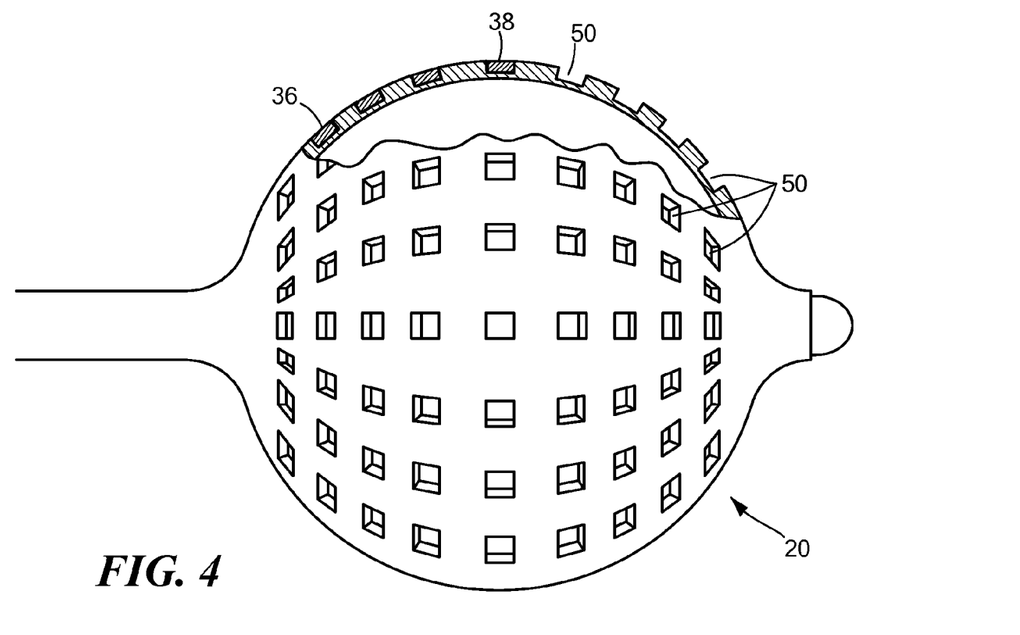
FIG. 4 is a side view of the medical device of FIG. 1 with recessed electrodes on the expandable element's surface.

Referring now to FIG. 4, the expandable element 24 may define a recess 50 sized to receive one or more of the electrodes 36 or 38 such that the each electrode 36 or 38 is flush with the surface of the expandable element 24. In a particular configuration, a plurality of recesses 50 are defined on the surface of the balloon and sized to receive a single electrode 36 or 38 such that the single electrode 36 or 38 retained within the recess 50 is substantially co-planar with the surface of the balloon. The electrodes 36 or 38 may be glued, embedded, or otherwise affixed to the balloon within the recess 50 such that during inflation and deflation of the balloon the electrodes 36 or 38 do not become dislodged. In an exemplary configuration, the one or more wires 46 may also be embedded within the balloon such that each wire 46 is substantially-coplanar with the surface of the balloon.

Figure 6:
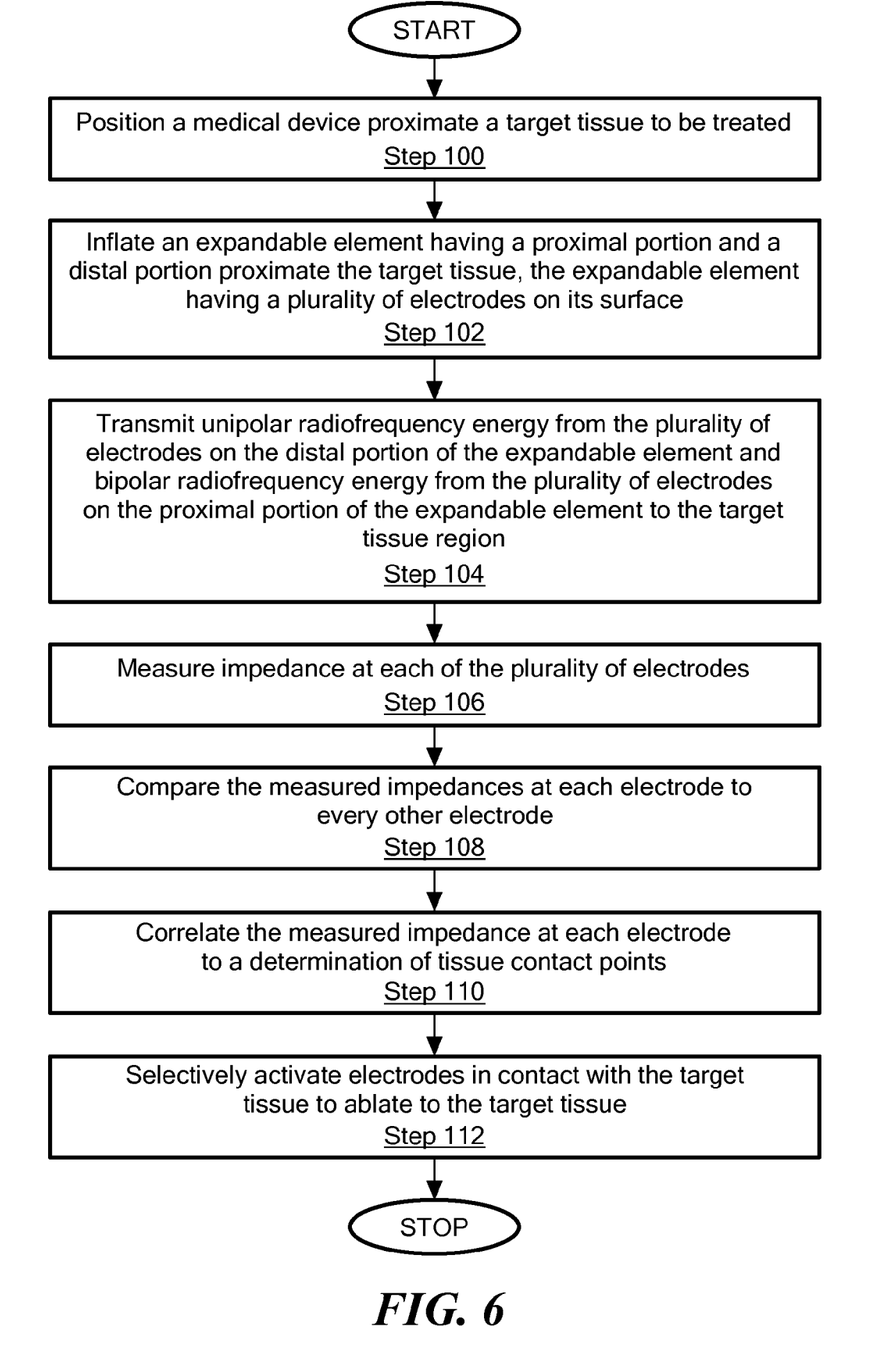
FIG. 6 is a method of operating the medical device shown in FIG. 1.

Now referring to FIG. 6, in which an exemplary method of tissue contact based tissue ablation is shown, the method includes positioning the medical device 12 proximate a target tissue to be treated (Step S100). For example, the medical device 12 may be placed within or proximity to a blood vessel, nervous, or cardiac tissue for diagnostic and/or ablation procedures. The expandable element 24 may inflated proximate or within the tissue to be treated (Step S102). For example, saline may be circulated through the inflation lumen, in a bolus or continuous flow, to inflate the expandable element 24. The shape of the expandable element 24 may be adjusted by a pull wire (not shown) or by varying or directing the flow of fluid within the expandable element 24 to accommodate a particular tissue in the body. For example, the expandable element 24 may be selectively shapeable to form an elongate expanded shape to fit within a narrow vein or may define a substantially spherical shape to perform blotting procedures.

The first plurality of electrodes 36 and the second plurality of electrodes 38 may then be activated to transmit radiofrequency energy to the target tissue region (Step S104). For example, each and every electrode 36, 38 on the expandable member 24 may be activated to measure impedance either between adjacent electrodes 38 or between each electrode 36 and a reference electrode to map the tissue region surrounding the expandable element (Step S106). The activation of the first plurality of electrodes 36 and the second plurality of electrodes 38 may be simultaneously or sequentially. Alternatively, particular regions of the expandable element 24 may be activated in sequence or depending on the particular tissue to be treated. For example, the electrode arrays 48 or electrodes 36 disposed within the distal portion 34 may be activated to obtain an impedance of tissue proximate the distal portion 34, followed by activation of the electrode arrays 48 or electrodes 38 in the proximal portion 30 and/or intermediate portion 32. In particular, unipolar radiofrequency energy may be transmitted by electrodes 36 in the distal portion 34 either sequentially or simultaneously with the transmission of bipolar radiofrequency energy from electrodes 38 in the proximal portion 30 and/or intermediate portion 32. Alternatively, the transmission of unipolar and/or bipolar radiofrequency energy may be programmed based on the particular blood vessel or tissue the expandable element 24 is disposed within. For example, the operator may preprogram particular electrodes 36 and/or 38 to activate and measure impedance at different times and at different locations within the blood vessel. In particular, as the expandable element 24 is moved to a different location within the blood vessel to measure impedance or ablate tissue, certain pre-selected electrodes 36 or 38 may activate to minimize interference from other electrodes 36 and 38 within the array and improve the accuracy of the mapping or ablation procedure. Because of the grid-like positioning of the electrodes 36 and 38 on the surface of the expandable element 24, the spatial resolution between electrodes may be greater than traditional mapping procedures such that the tissue contact points can be accurately identified. For example, the impedance measurements recorded for each electrode 36, 38 may be compared against every other electrode 36, 38 to detect a variance in impedance measurements associated with each electrode (Step S108). The impedance variation may be dependent upon the size and geometry of the electrodes 36, 38. With intimate tissue contact (i.e. the expandable element 24 insulating the electrodes 36, 38 from the surrounding blood pool), the impedance may vary by 50-100 ohms between an electrode 36 or 28 in contact with the tissue and one in the blood pool. Contact may also be identified by monitoring a jump in the impedance of each individual electrode 36, 38.

Because of the large sample size of electrodes 36, 38 to be compared, small differences in the measured impedances may indicate, for example, tissue contact points. For example, impedance measurements recorded at each electrode 36, 38 and/or each array 48 may be either compared against a threshold impedance value to indicate tissue contact or may be compared against each other to determine a variance at any one electrode. The threshold may be a particular value or a percentage over or under a particular value depending on the treatment site. Additionally, electrograms measured at the identified tissue contact points can detect complex fractionated atrial electrograms and/or rotors for possible ablation sites simultaneously or sequentially with the measurement of impedance. Based on the comparison of the measured impedances, tissue contact and ablation points may be identified and correlated to a particular electrode (Step 110). For example, if the measured impedances are above a predetermined threshold at a particular electrode 36 or 38, the identified electrode 36 or 38 may be independently and selectively activated to transmit unipolar or bipolar radiofrequency to ablation the tissue in contact with the electrodes 36, 38 (Step 112). As such, energy may be conserved because electrodes 36 or 28 not in contact with tissue may not be activated. Alternatively, once the tissue contact points are identified in Step S110, other modalities of ablation may be utilized to ablate the tissue in contact with the identified electrodes. For example, cryogenic fluid may flow into the expandable element 24 and may be directed by a sprayer (not shown) disposed within the expandable element 24 toward the areas of the expandable element 24 in contact with the expandable element 24.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of ablating a target tissue region, comprising:
    positioning a medical device having an expandable element proximate the target tissue region, the expandable element including a first plurality of electrodes coupled to a distal portion of the expandable element, and a second plurality of electrodes coupled to a proximal portion of the expandable element;
    transmitting unipolar radiofrequency energy from the first plurality of electrodes and simultaneously transmitting bipolar radiofrequency energy from the second plurality of electrodes;
    measuring an impedance from each electrode of the first plurality of electrodes;
    measuring an impedance from each electrode of the second plurality of electrodes;
    comparing the measured impedance from each electrode of the first plurality of electrodes and the second plurality of electrodes;
    identifying areas of tissue that are in contact with at least some of the first plurality of electrodes and the second plurality of electrodes based on the comparison; and
    activating the at least some of the first plurality of electrodes and the second plurality of electrodes that are in contact with the tissue to ablate the tissue.

2. The method of claim 1, wherein ablating tissue in contact with the expandable element includes selectively operating at least one electrode of the first plurality of electrodes and at least one electrode of the second plurality of electrodes in contact with the expandable element and transmitting radiofrequency energy to the target tissue region.

3. The method of claim 1, wherein ablating tissue in contact with the expandable element includes delivering cryogenic fluid to the expandable element and exchanging cryogenic energy with the target tissue region.

4. The method of claim 1, wherein the first plurality of electrodes are substantially coplanar with the exterior surface of the expandable element.

5. The method of claim 1, wherein the second plurality of electrodes are substantially coplanar with the exterior surface of the expandable element.

6. The method of claim 1, wherein the expandable element is selectively shapeable.

7. The method of claim 1, wherein the first plurality of electrodes and the second plurality of electrodes are arranged in a substantially linear array on the exterior surface of the expandable element.

8. The method of claim 1, wherein the expandable element defines a plurality of recesses on the exterior surface, and wherein each recess is sized to receive one electrode of at least one of the first plurality of electrodes and the second plurality of electrodes.

9. The medical device of claim 1, wherein the expandable element is a balloon.

10. A medical system, comprising:
    a medical device, the medical device including:
        a catheter including a proximal end and a distal end;
        an expandable element coupled to the distal end, the expandable element including a proximal portion and a distal portion, the expandable element defining an exterior surface;
        a first plurality of electrodes coupled to the exterior surface of the distal portion of the expandable element, each of the first plurality of electrodes being selectively operable to transmit unipolar radiofrequency energy;
        a second plurality of electrodes coupled to the exterior surface of the proximal portion of the expandable element, each of the second plurality of electrodes being selectively operable to transmit bipolar radiofrequency energy, the first plurality of electrodes and the second plurality of electrodes together defining a grid of axially aligned electrodes that covers substantially the entire exterior surface of the expandable element; and
    a control unit having a processor, the processor being operable to:
        transmit unipolar radiofrequency energy from the first plurality of electrodes and simultaneously transmit bipolar radiofrequency energy from the second plurality of electrodes;
        measure an impedance from each electrode of the first plurality of electrodes;
        measure an impedance from each electrode of the second plurality of electrodes;
        compare the measured impedance from each electrode of the first plurality of electrodes and the second plurality of electrodes;
        identify tissue contact areas based on the comparison; and
        ablate tissue in contact with the expandable element based on the comparison.

* * * * *